(12) United States Patent
Fuseya et al.

(10) Patent No.: US 11,896,790 B2
(45) Date of Patent: Feb. 13, 2024

(54) DILATOR

(71) Applicant: ASAHI INTECC CO., LTD., Seto (JP)

(72) Inventors: Yukihiro Fuseya, Seto (JP); Marina Tsuzuku, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 260 days.

(21) Appl. No.: 17/205,789

(22) Filed: Mar. 18, 2021

(65) Prior Publication Data

US 2021/0205591 A1 Jul. 8, 2021

Related U.S. Application Data

(63) Continuation of application No. PCT/JP2018/035090, filed on Sep. 21, 2018.

(51) Int. Cl.
*A61M 29/00* (2006.01)
*A61M 25/00* (2006.01)

(52) U.S. Cl.
CPC ....... *A61M 29/00* (2013.01); *A61M 2025/006* (2013.01)

(58) Field of Classification Search
CPC ...... A61B 2017/320056; A61M 29/00; A61M 2025/006; A61M 25/01; A61M 2025/0687
See application file for complete search history.

(56) References Cited

U.S. PATENT DOCUMENTS

| | | |
|---|---|---|
| 4,491,126 A | 1/1985 | Cullor |
| 4,629,450 A | 12/1986 | Suzuki et al. |
| 5,279,567 A * | 1/1994 | Ciaglia ............... A61B 17/3415 604/117 |
| 5,403,336 A | 4/1995 | Kieturakis et al. |
| 9,393,006 B2 * | 7/2016 | Housman ............. A61B 17/861 |
| 9,901,379 B2 * | 2/2018 | Reed ................... A61B 17/866 |
| 11,578,747 B2 * | 2/2023 | Gong .................. F16B 25/0052 |
| 2001/0047175 A1 * | 11/2001 | Doubler ............. A61B 17/8635 606/301 |
| 2002/0077655 A1 | 6/2002 | Frova |
| 2004/0184897 A1 * | 9/2004 | Levey ..................... F16B 39/30 411/411 |
| 2007/0088230 A1 | 4/2007 | Terashi et al. |

(Continued)

FOREIGN PATENT DOCUMENTS

| | | |
|---|---|---|
| EP | 0 542 103 A1 | 5/1993 |
| EP | 1 731 105 | 12/2006 |

(Continued)

*Primary Examiner* — Phong Son H Dang
(74) *Attorney, Agent, or Firm* — Oliff PLC

(57) ABSTRACT

A dilator that includes a shaft and a spirally-arranged protruding portion. The shaft includes a tapered section, a distal end section, and a body section. The spirally-arranged protruding portion includes spirally-arranged protruding sections provided on outer peripheral surfaces of each of the tapered section, the distal end section, and the body section, and gaps between adjacent spirally-arranged protruding sections along an axial direction of the shaft. At least one of a height t of the spirally-arranged protruding portion at a first location gradually decreases toward a distal end side and a height of the spirally-arranged protruding portion at a second location gradually decreases toward a proximal end side.

15 Claims, 15 Drawing Sheets

(56) References Cited

U.S. PATENT DOCUMENTS

| | | | |
|---|---|---|---|
| 2007/0142837 A1* | 6/2007 | Dreyfuss | A61B 17/0401 606/232 |
| 2011/0092909 A1 | 4/2011 | Andersson et al. | |
| 2012/0010598 A1* | 1/2012 | Frassica | A61M 25/0068 604/528 |
| 2012/0029281 A1 | 2/2012 | Frassica et al. | |
| 2012/0149985 A1* | 6/2012 | Frassica | A61B 1/00082 600/137 |
| 2013/0274782 A1 | 10/2013 | Morgan | |
| 2014/0046357 A1* | 2/2014 | Neoh | A61M 29/00 606/191 |
| 2014/0058460 A1* | 2/2014 | Reed | A61B 17/863 606/301 |
| 2015/0073429 A1 | 3/2015 | Sartor et al. | |
| 2015/0164552 A1 | 6/2015 | Chen et al. | |
| 2017/0202575 A1 | 7/2017 | Stanfield et al. | |

FOREIGN PATENT DOCUMENTS

| | | |
|---|---|---|
| EP | 3804642 A1 | 4/2021 |
| JP | S60-234671 A | 11/1985 |
| JP | 2002-177289 A | 6/2002 |
| JP | 2007-098120 A | 4/2007 |
| JP | 5448200 B2 | 3/2014 |
| JP | 2014-524807 A | 9/2014 |
| JP | 5582612 B2 | 9/2014 |
| JP | 2017-523019 A | 8/2017 |
| WO | 2006/071785 A2 | 7/2006 |
| WO | 2013/038720 A1 | 3/2013 |
| WO | 2018-180209 A1 | 10/2018 |

\* cited by examiner

[FIG. 1]
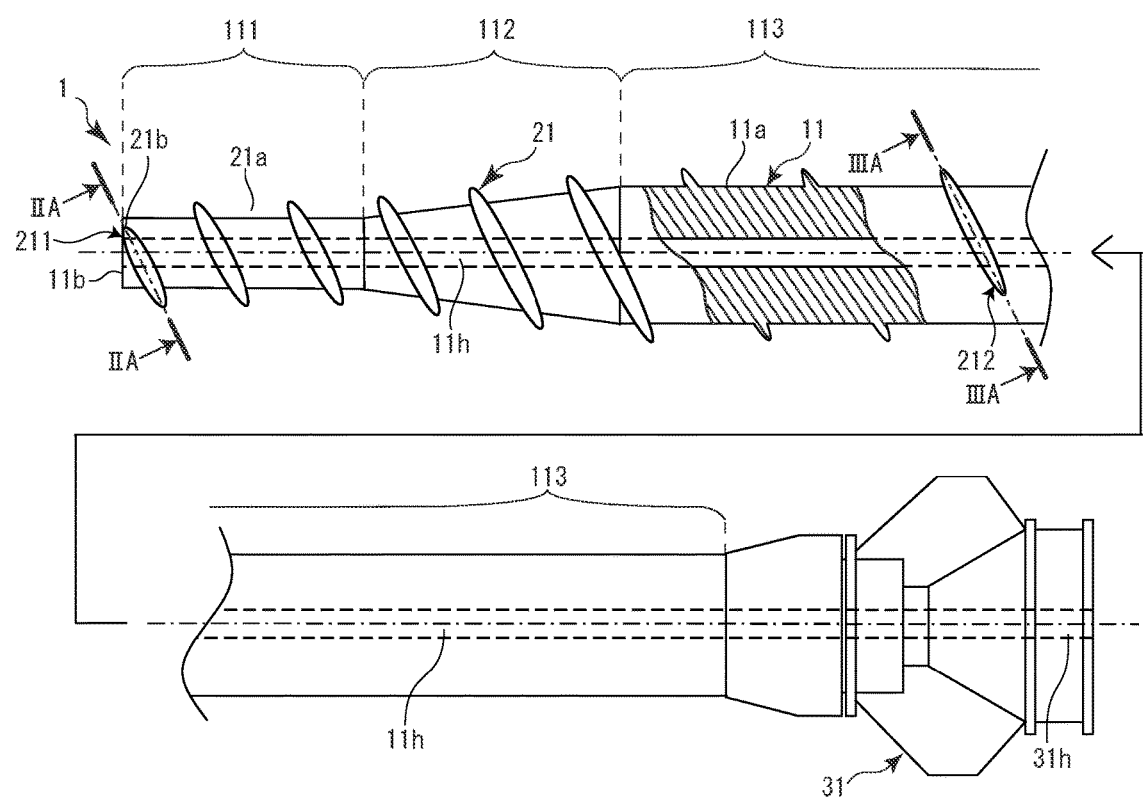

[FIG. 2A]
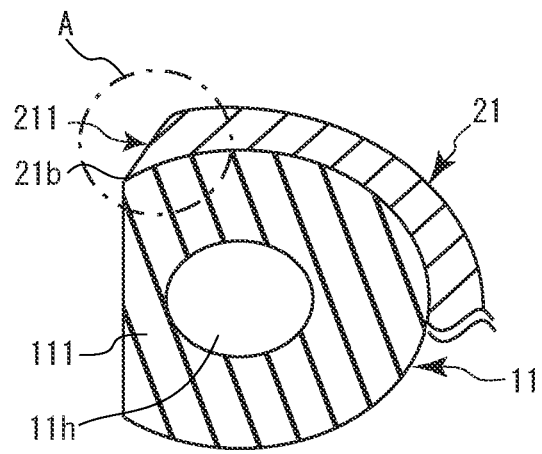
[FIG. 2B]
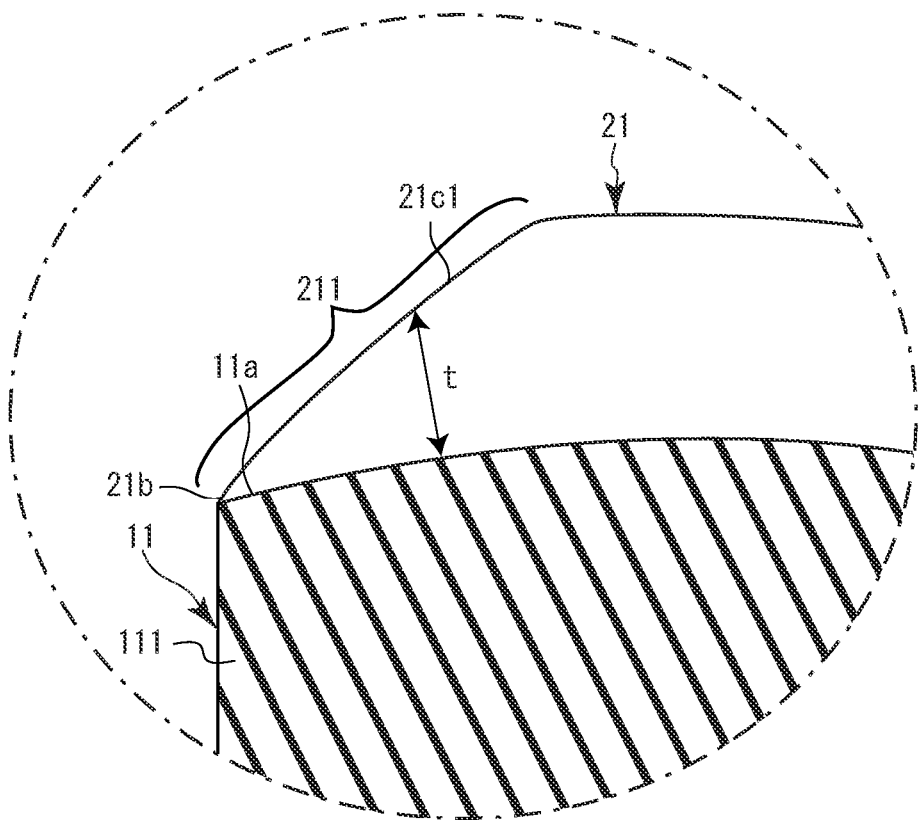

[FIG. 3A]
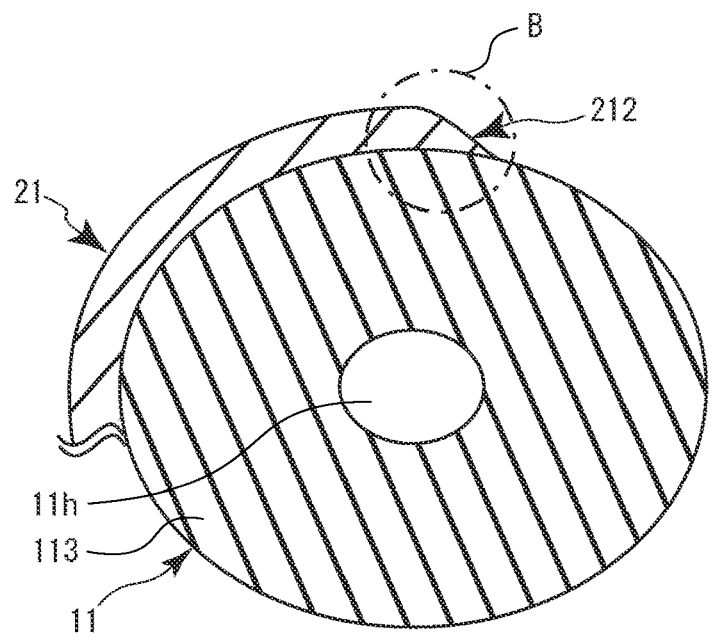
[FIG. 3B]
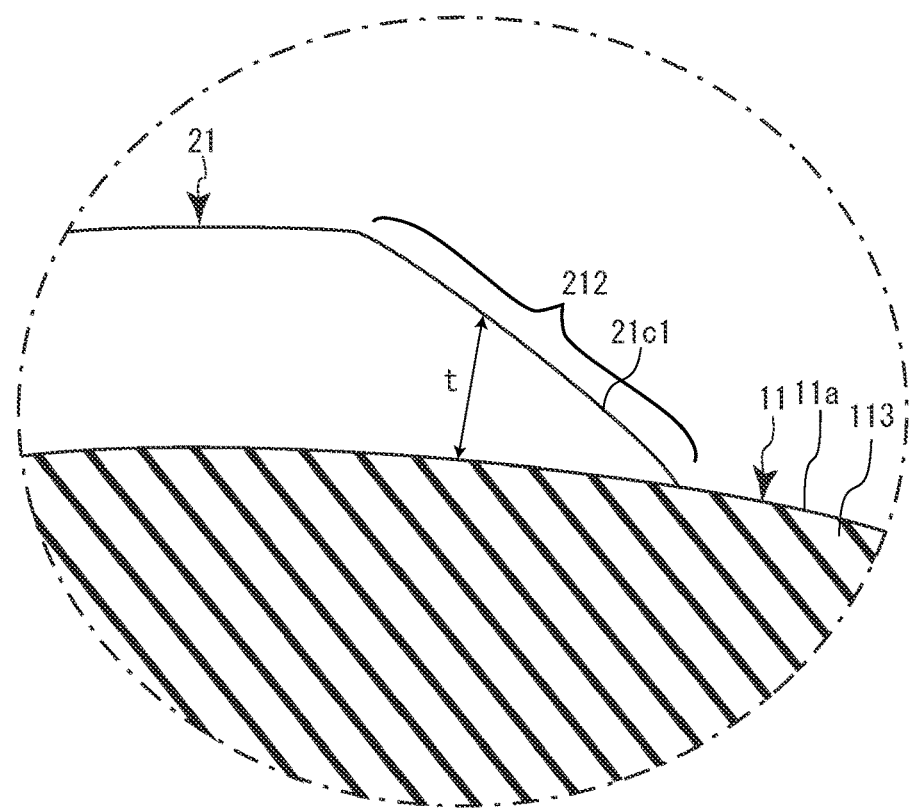

[FIG. 4A]
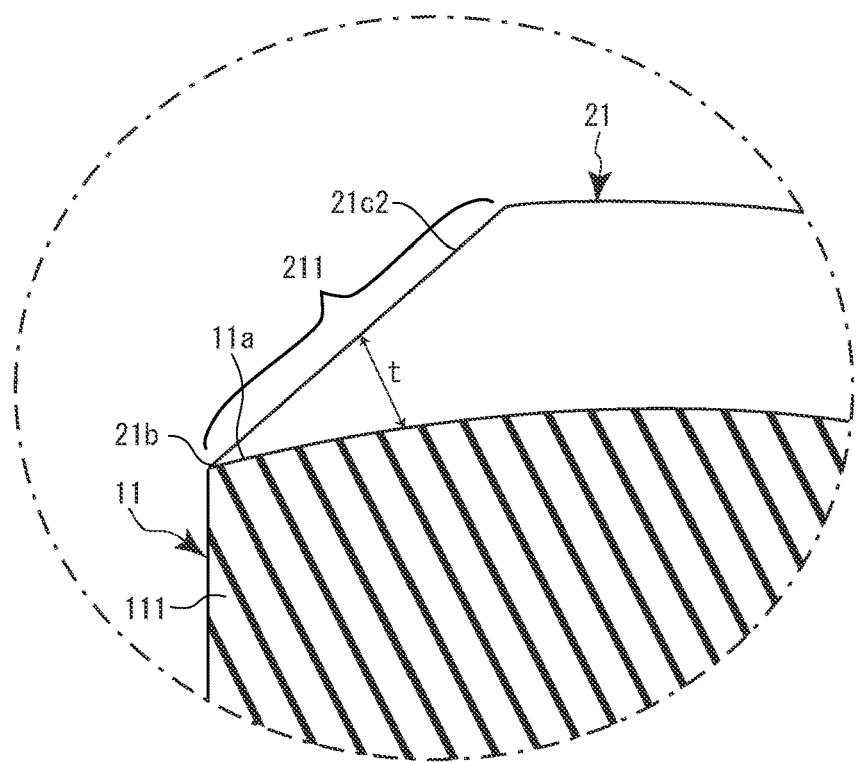
[FIG. 4B]
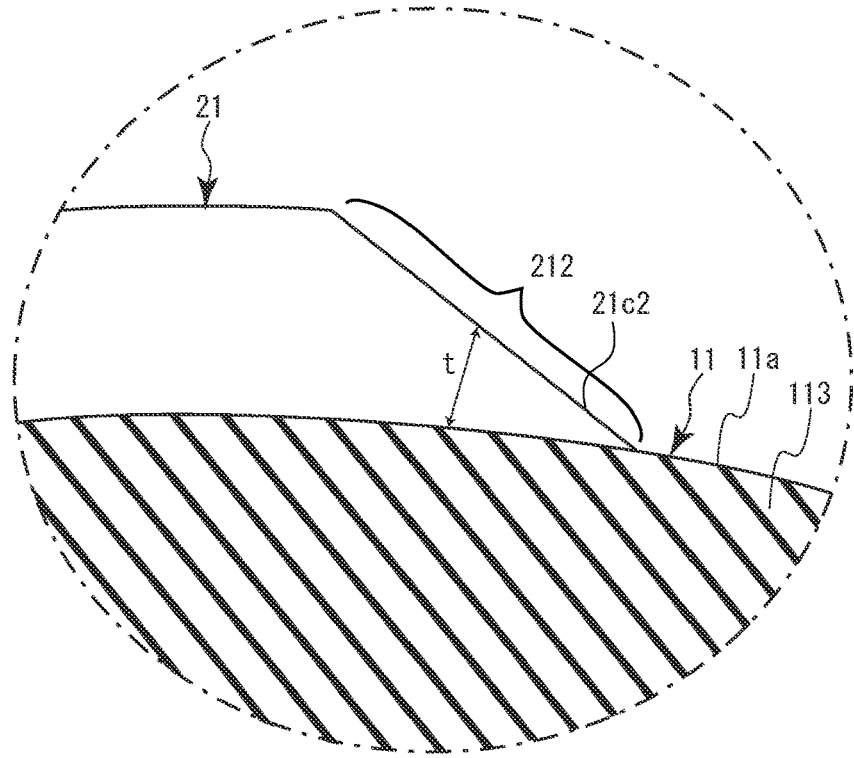

[FIG. 4C]
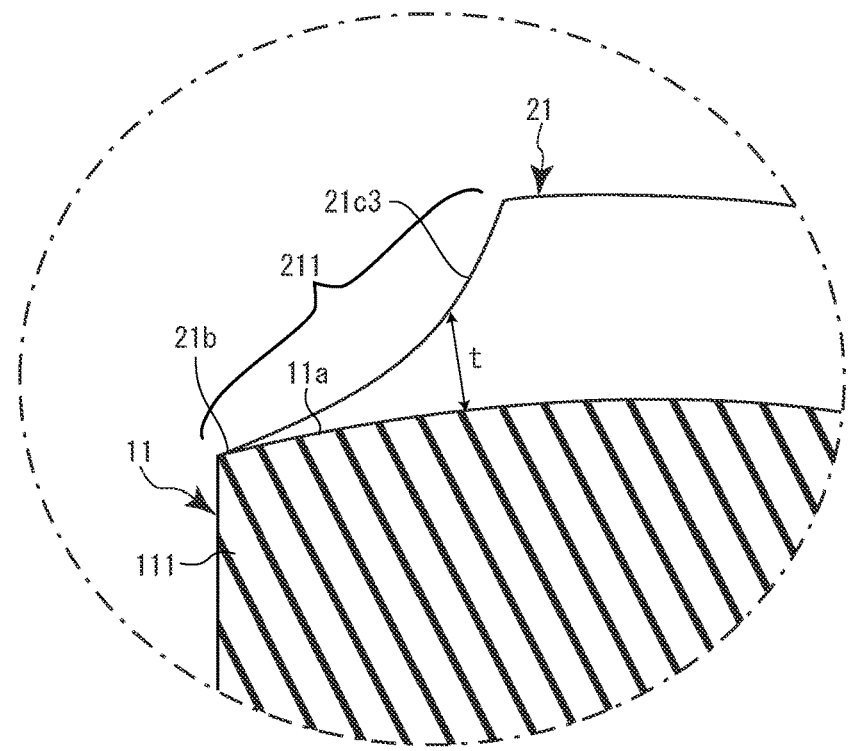
[FIG. 4D]
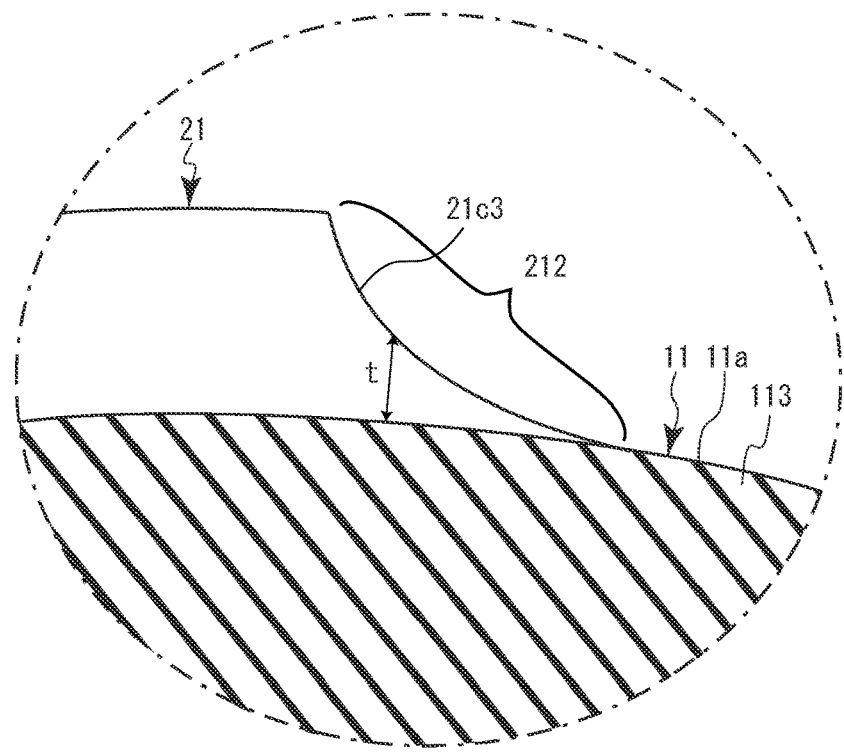

[FIG. 4E]
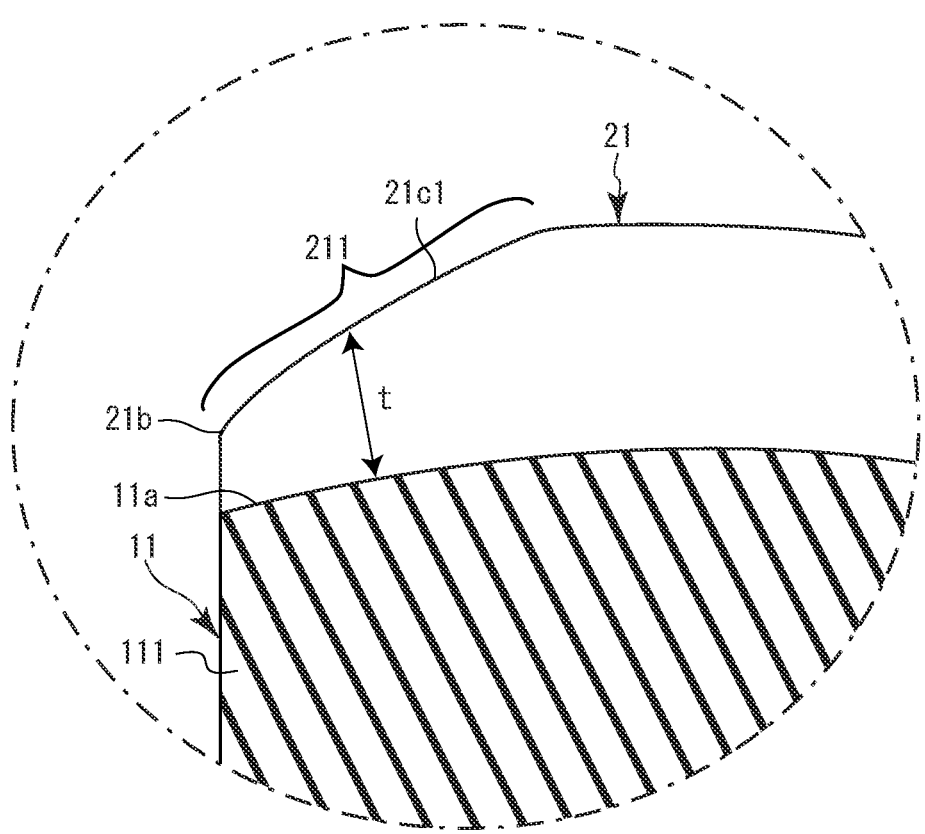

[FIG. 5]
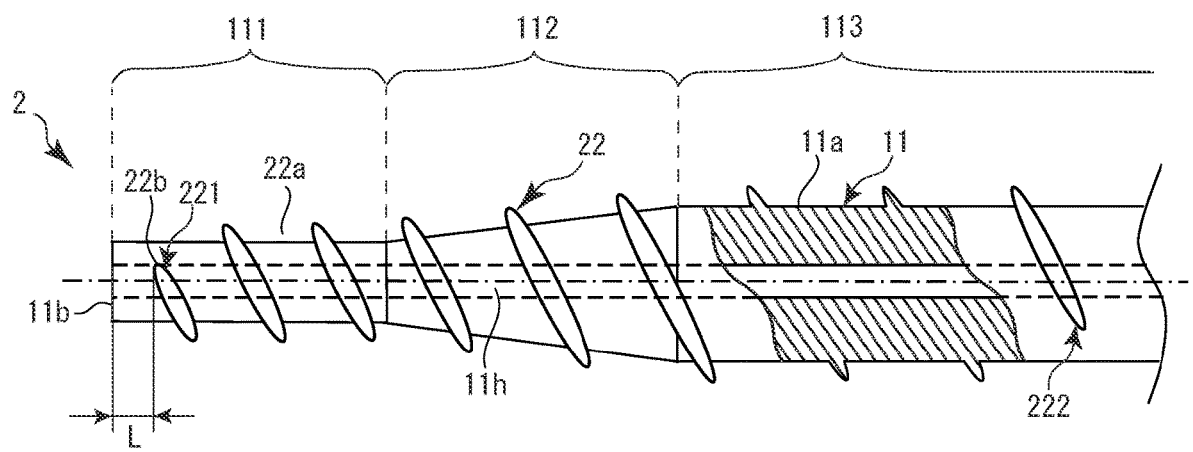

[FIG. 6]
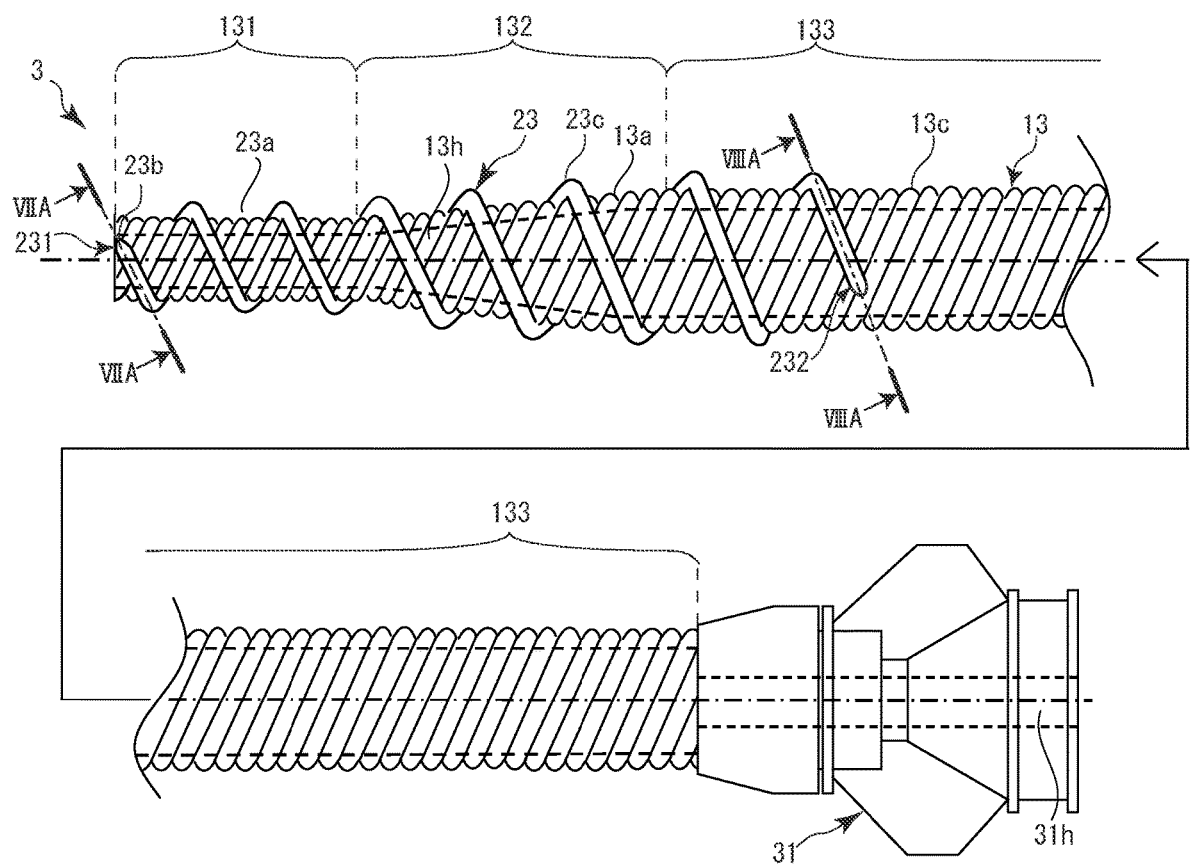

[FIG. 7A]
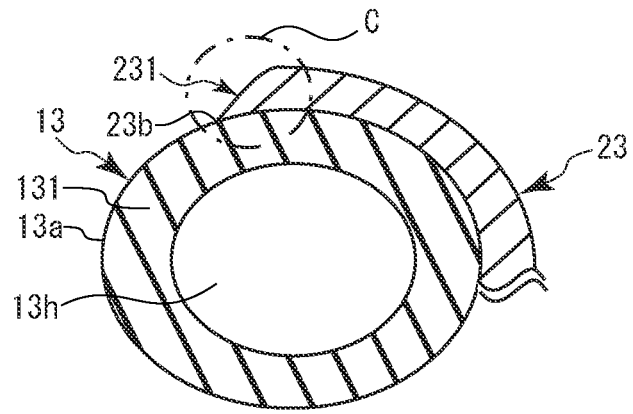
[FIG. 7B]
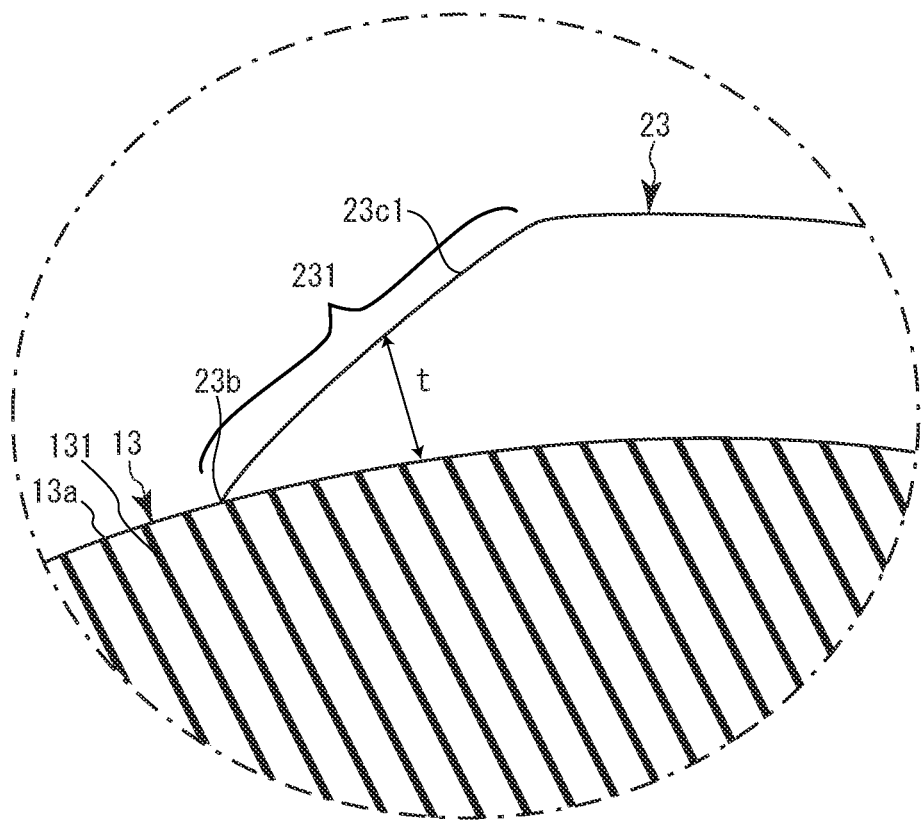

[FIG. 8A]
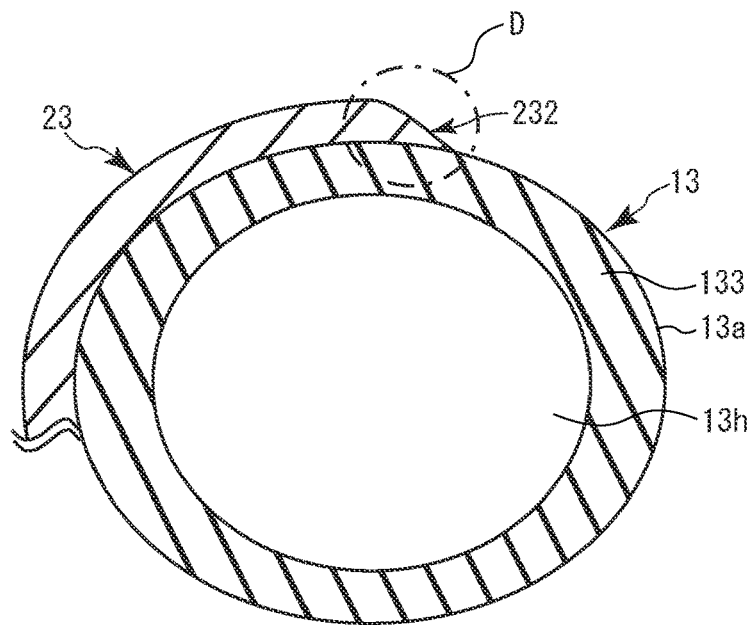
[FIG. 8B]
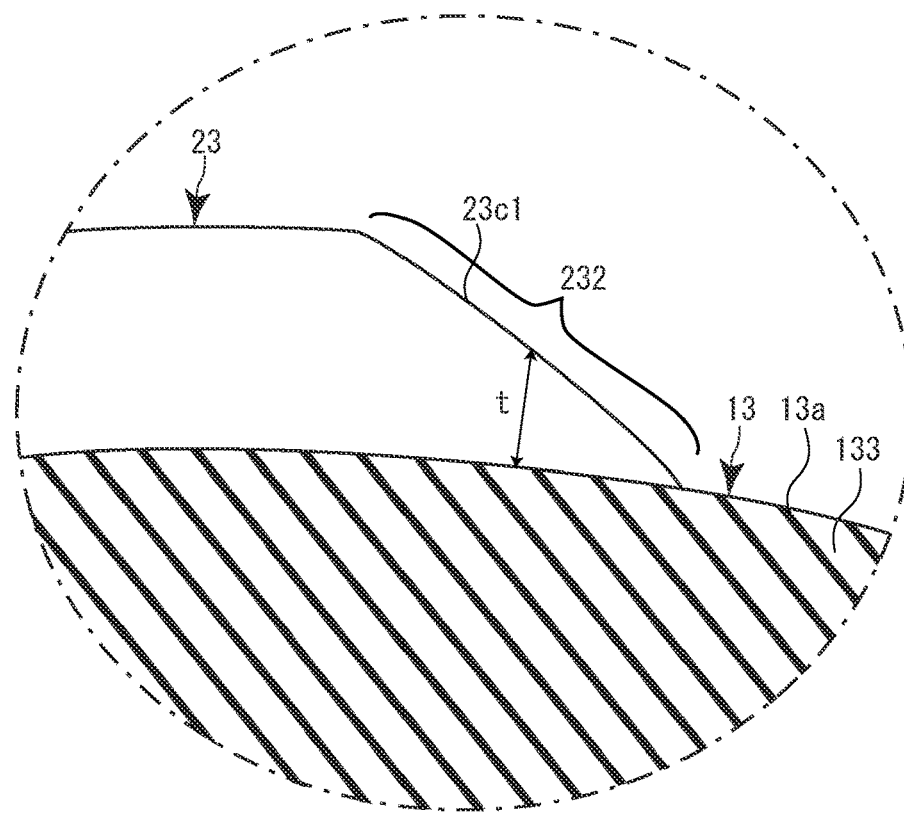

[FIG. 9]
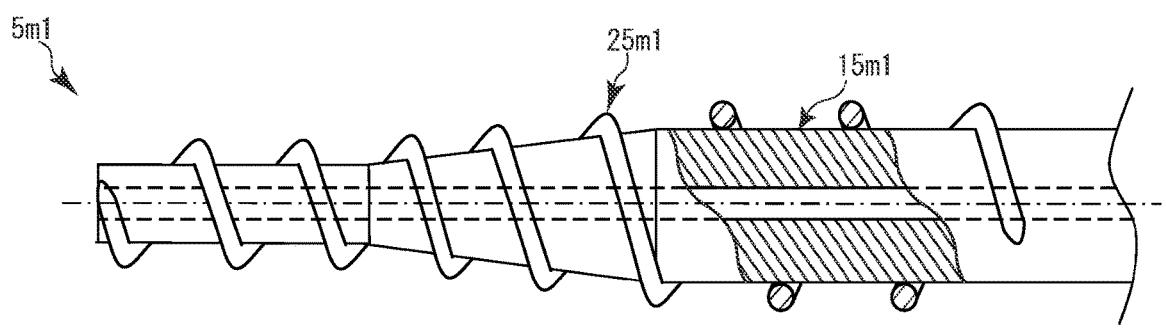

[FIG. 10A]
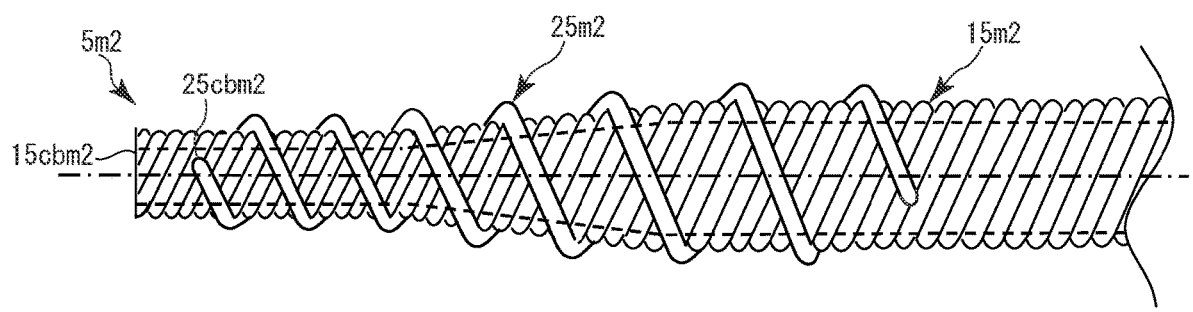

[FIG. 10B]
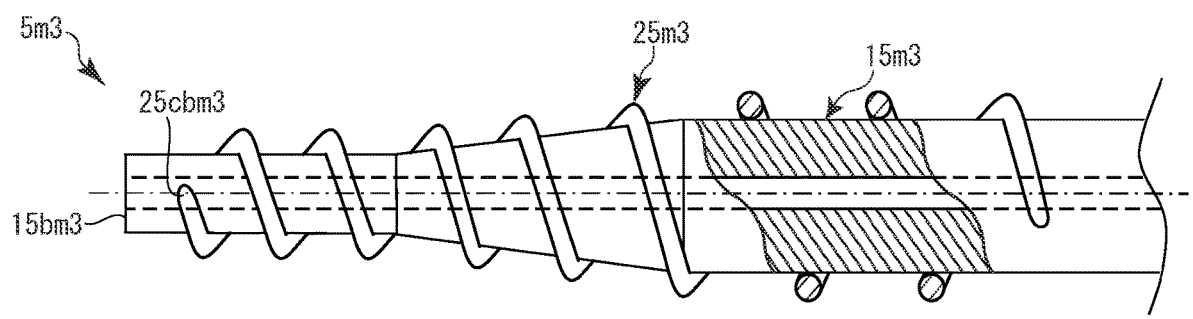

[FIG. 11A]
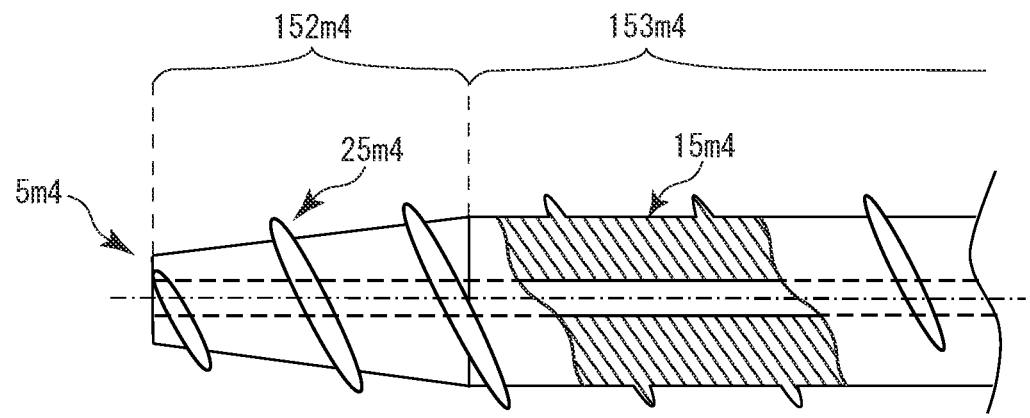
[FIG. 11B]
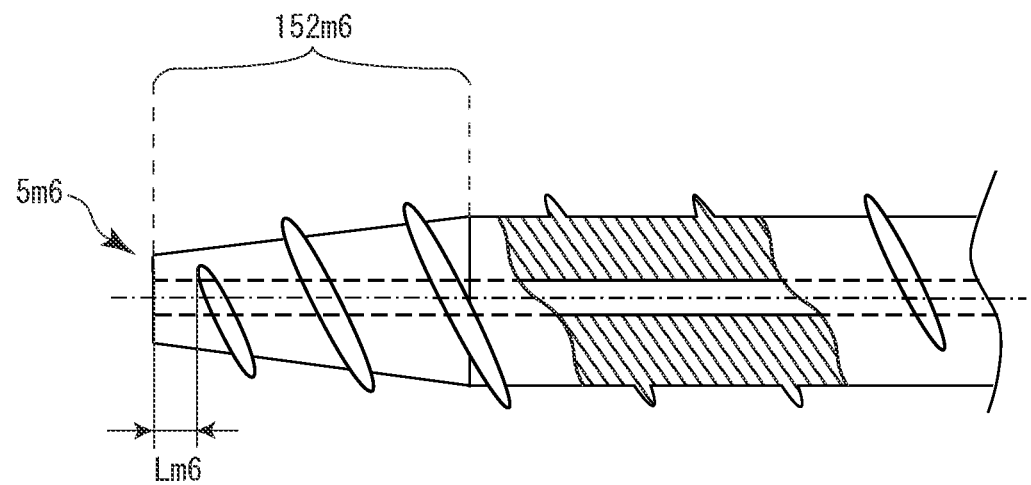

[FIG. 12A]
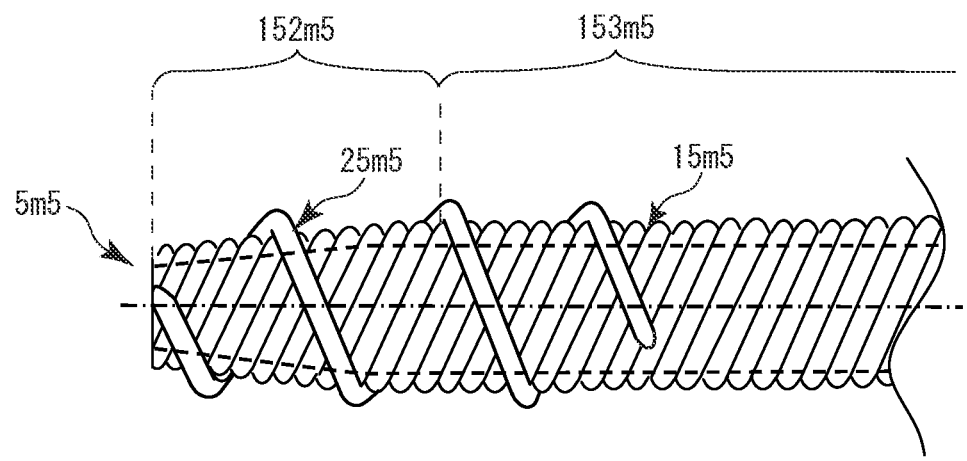
[FIG. 12B]
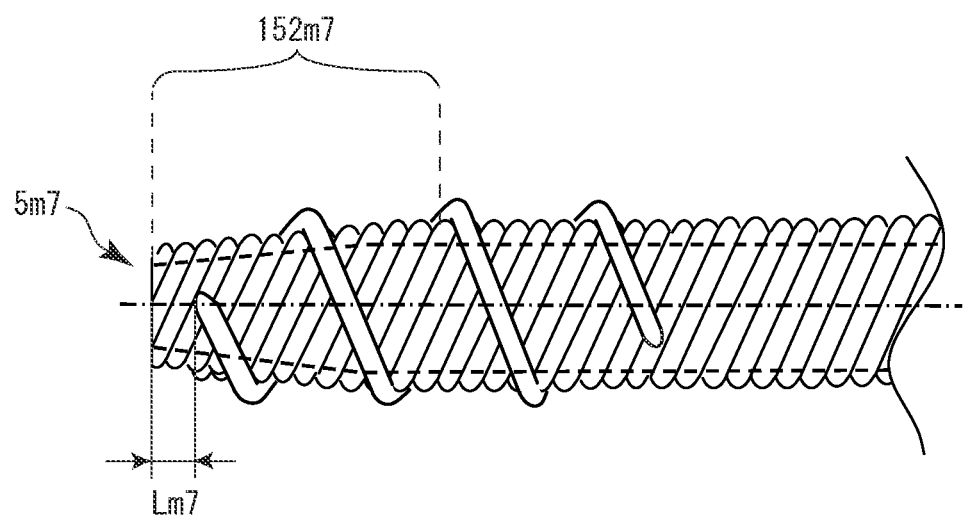

DILATOR

CROSS REFERENCE TO RELATED APPLICATION

This application is a continuation application of International Application No. PCT/JP2018/035090, filed Sep. 21, 2018. The contents of this application are incorporated herein by reference in their entirety.

BACKGROUND

This application relates to a dilator.

There are known dilators for dilating a hole formed in a wall of a lesioned region in a gastrointestinal tract of a patient for treatment. Such a dilator dilates the hole by inserting a distal end of the dilator into the hole formed in the wall and pushing a tapered section into the hole, as discussed in Japanese Patent Document JP 2002-177289.

Specifically, in the dilator described above, a screw thread is provided in the tapered section of a rod. The dilator is rotated and the screw thread is caught on the wall of the lesioned region, so that a propulsive force is generated in the dilator.

However, in these dilators, shapes of ends (a distal end and a proximal end) of the screw thread are not sufficiently considered, and, by way of example, when the rod is screwed into the hole or the like, the distal end of the screw thread acts as a resistance, and therefore, smooth insertion of the rod into the hole or the like may possibly be hindered.

SUMMARY

The disclosed embodiments have been made based on the above circumstances, and an object thereof is to provide a dilator capable of smoothly advancing and retreating a shaft when the shaft (rod) is inserted into or removed from a hole, a constricted part, or the like formed in a wall of an organ or the like (hereinafter, also referred to as "hole of a target object").

To achieve the above object, a dilator according to an embodiment of the present disclosure includes: a dilator including a hollow-shaped shaft and spirally-arranged protruding portion, in which:

(1) the shaft includes a tapered section with an outer diameter of a distal end being smaller than an outer diameter of a proximal end, a distal end section including a proximal end being located at the distal end of the tapered section and extending toward a distal end side of the tapered section in an axial direction, and a body section including a distal end being located at the proximal end of the tapered section and extending toward a proximal end side of the tapered section in the axial direction, (2) the spirally-arranged protruding portion is provided on each outer peripheral surface of the tapered section, the distal end section, and the body section and includes gaps between neighboring sections of the spirally-arranged protruding portion along the axial direction of the shaft, (3) a location being at a distal end side in the spirally-arranged protruding portion and including a distal end of the spirally-arranged protruding portion is a first location and a location being at a proximal end side in the spirally-arranged protruding portion and at the proximal end side relative to the first location and including a proximal end of the spirally-arranged protruding portion is a second location, and (4) a height of the spirally-arranged protruding portion at the first location gradually decreases toward the distal end side and/or a height of the spirally-arranged protruding portion at the second location gradually decreases toward the proximal end side.

It is noted that as used herein, the "distal end side" refers to a direction along the axial direction of the shaft and a direction in which the tapered section is located with respect to the body section. Further, the "proximal end side" refers to a direction along the axial direction of the dilator and a direction opposite to the distal end side. Further, the "distal end" refers to an end at the distal end side in any member or location, and the "proximal end" refers to an end at the proximal end side in any member or location, respectively. Further, the "height of the protrusion" refers to a dimension from the outer peripheral surface of the shaft where the spirally-arranged protruding portion is located to an outer peripheral end of the spirally-arranged protruding portion, in a front view in the axial direction of the shaft, in a radial direction (a direction perpendicular to a tangent of the outer peripheral surface of the shaft) of the shaft, and specifically, by way of example, refers to the height t of the spirally-arranged protruding portion, as illustrated in the drawings.

BRIEF DESCRIPTION OF THE DRAWINGS

FIG. 1 is a partially cut schematic side view entirely illustrating a dilator of the disclosed embodiments;

FIG. 2A is a schematic end view cut along line IIA-IIA of FIG. 1;

FIG. 2B is an enlarged schematic view of a part A in FIG. 2A;

FIG. 3A is a schematic end view cut along line IIIA-IIIA of FIG. 1;

FIG. 3B is an enlarged schematic view of a part B in FIG. 3A;

FIG. 4A is an enlarged schematic view illustrating a first location of a spirally-arranged protruding portion of a dilator of the disclosed embodiments;

FIG. 4B is an enlarged schematic view illustrating a second location of a spirally-arranged protruding portion of a dilator of the disclosed embodiments;

FIG. 4C is an enlarged schematic view illustrating a first location of a spirally-arranged protruding portion of a dilator of the disclosed embodiments;

FIG. 4D is an enlarged schematic view illustrating a second location of a spirally-arranged protruding portion of a dilator of the disclosed embodiments;

FIG. 4E is an enlarged schematic view illustrating a first location of a spirally-arranged protruding portion of a dilator of the disclosed embodiments;

FIG. 5 is a partially cut schematic side view illustrating a part of a dilator of the disclosed embodiments;

FIG. 6 is a schematic side view entirely illustrating a dilator of the disclosed embodiments;

FIG. 7A is a schematic end view cut along line VIIA-VIIA of FIG. 6;

FIG. 7B is an enlarged schematic view of a part C in FIG. 7A;

FIG. 8A is a schematic end view cut along line VIIIA-VIIIA of FIG. 6;

FIG. 8B is an enlarged schematic view of a part D in FIG. 8A;

FIG. 9 is a partially cut schematic side view illustrating a part of a dilator of the disclosed embodiments;

FIG. 10A is a schematic side view illustrating a part of a dilator of the disclosed embodiments;

FIG. 10B is a partially cut schematic side view illustrating a part of a dilator of the disclosed embodiments;

FIG. 11A is a partially cut schematic side view illustrating a part of a dilator of the disclosed embodiments;

FIG. 11B is a partially cut schematic side view illustrating a part of a dilator of the disclosed embodiments;

FIG. 12A is a schematic side view illustrating a part of a dilator of the disclosed embodiments; and FIG. 12B is a schematic side view illustrating a part of a dilator of the disclosed embodiments.

DETAILED DESCRIPTION

In the disclosed embodiments, the dilator is a dilator provided with a hollow-shaped shaft and a spirally-arranged protruding portion. The shaft includes a tapered section with an outer diameter of a distal end being smaller than an outer diameter of a proximal end, a distal end section including a proximal end being located at the distal end of the tapered section and extending toward a distal end side of the tapered section in an axial direction, and a body section including a distal end being located at the proximal end of the tapered section and extending toward a proximal end side of the tapered section in the axial direction. The spirally-arranged protruding portion is provided on an outer peripheral surface of each of the tapered section, the distal end section, and the body section and includes gaps between neighboring sections of the spirally-arranged protruding portion along the axial direction of the shaft. A location being at a distal end side in the spirally-arranged protruding portion and including a distal end of the spirally-arranged protruding portion is a first location and a location being at a proximal end side in the spirally-arranged protruding portion and at the proximal end side relative to the first location and including a proximal end of the spirally-arranged protruding portion is a second location. A height of the spirally-arranged protruding portion at the first location gradually decreases toward the distal end side and/or a height of the spirally-arranged protruding portion at the second location gradually decreases toward the proximal end side.

The present disclosure will be described below with reference to the drawings, but the disclosed embodiments are not intended to be limited only to the embodiments described in the drawings. Further, the dimensions of the dilator illustrated in each drawing are dimensions indicated to facilitate the understanding of the contents of implementation and may not correspond to the actual dimensions.

FIG. 1 is a partially cut schematic side view entirely illustrating a dilator of the disclosed embodiments. As illustrated in FIG. 1, dilator 1 generally includes a shaft 11, a spirally-arranged protruding portion 21, and a base section 31.

The shaft 11 is a hollow-shaped member. Specifically, the shaft 11 includes, for example, a hollow-shaped through-hole 11h, and the through-hole 11h forms a continuous space connecting a distal end and a proximal end of the shaft 11. For example, a guide wire (not illustrated) or the like is inserted into the through-hole 11h. Further, the shaft 11 includes a distal end section 111, a tapered section 112, and a body section 113.

The distal end section 111 is a section of which a proximal end is located at a distal end of the tapered section 112 described later, and which extends toward a distal end side of the tapered section 112 in an axial direction. Specifically, the distal end section 111 is formed so that, for example, the proximal end of the distal end section 111 is continuous with the distal end of the tapered section 112 and the distal end section 111 has a substantially constant outer diameter from the distal end to the proximal end.

The tapered section 112 is a section of which an outer diameter of the distal end is smaller than an outer diameter of the proximal end. The tapered section 112 has a shape that tapers from the proximal end to the distal end (the outer diameter of the distal end is smaller than the outer diameter of the proximal end). As a result, when the shaft 11 is pushed forward, a hole or the like of a target object is dilated by the tapered section 112.

The body section 113 is a section of which a distal end is located at the proximal end of the tapered section 112 and which extends toward a proximal end side of the tapered section 112 in the axial direction. Specifically, for example, the body section 113 has a substantially constant outer diameter from the distal end of the body section 113 to the proximal end thereof, and the base section 31 described later is connected to the proximal end.

It is noted that the distal end section 111 and the tapered section 112, and the tapered section 112 and the body section 113, described above may be formed integrally or separately, respectively. In the dilator 1, the distal end section 111, the tapered section 112, and the body section 113 are formed integrally by casting or the like.

The shaft 11 (the distal end section 111, the tapered section 112, and the body section 113) is inserted into a body cavity, and thus, the shaft 11 is preferably formed of a material having an antithrombotic property, flexibility, and biocompatibility, and examples of the material include a resin material such as a polyamide resin, a polyolefin resin, a polyester resin, a polyurethane resin, a silicone resin, and a fluororesin; and a metal material such as stainless steel and a superelastic alloy (a nickel-titanium alloy).

It is noted that the shaft 11 may have various types of coatings at an outer peripheral surface 11a. Examples of the coatings include a protective film (a representative example of which is a plating film) for protecting the surface of the shaft 11, and a base film for improving the adhesion between the outer peripheral surface 11a of the shaft 11 and the spirally-arranged protruding portion 21 described later.

The spirally-arranged protruding portions 21 are provided on the outer peripheral surface 11a of each of the distal end section 111, the tapered section 112, and the body section 113, and include gaps 21a between neighboring sections of the spirally-arranged protruding portion 21 along the axial direction of the shaft 11. The spirally-arranged protruding portion 21 protrudes radially outward from the outer peripheral surface 11a of the shaft 11 and neighboring spirally-arranged protruding portions 21 are distant in the axial direction, for example.

Here, the spirally-arranged protruding portion 21 includes a location 211 (hereinafter, also referred to as "first location 211") at the distal end side in the spirally-arranged protruding portion 21 and a location 212 (hereinafter, also referred to as "second location 212") at the proximal end side in the spirally-arranged protruding portion 21. The location 211 includes the distal end of the spirally-arranged protruding portion 21 and the location 212 is located at a proximal end side relative to the first location 211 and includes the proximal end of the spirally-arranged protruding portion 21. A height of the spirally-arranged protruding portion 21 at the first location 211 gradually decreases toward the distal end side of the spirally-arranged protruding portion 21 along the spirally-arranged protruding portion 21. A height of the spirally-arranged protruding portion 21 at the second location 212 gradually decreases toward the proximal end side of the spirally-arranged protruding portion 21 along the spirally-arranged protruding portion 21.

Specifically, as illustrated in FIGS. 2A and 2B, a height t of the spirally-arranged protruding portion 21 at the first location 211 may be formed so that the height t gradually decreases from a proximal end of the first location 211 toward a distal end 21*b* of the first location 211 (an outer peripheral surface 21*c*1 in a convex shape).

On the other hand, specifically, as illustrated in FIGS. 3A and 3B, for example, a height t of the spirally-arranged protruding portion 21 at the second location 212 may be formed so that the height t gradually decreases from a distal end of the second location 212 toward a proximal end of the second location 212 (the outer peripheral surface 21*c*1 in a convex shape).

Here, the dilator 1 is formed so that the height t of the distal end at the first location 211 and the height t of the proximal end at the second location 212 satisfy t=0 (in the radial direction of the shaft 11, a position of the spirally-arranged protruding portion 21 and a position of the outer peripheral surface 11*a* of the shaft 11 at the distal end and the proximal end of the spirally-arranged protruding portion 21 coincide). This enables a contact resistance to be reduced between the spirally-arranged protruding portion 21 and a contact object in a helical direction, and thus, it is possible to further smoothly advance and retreat the dilator 1

It is possible that in the dilator 1, a shape of the outer peripheral surface at at least one of the first location 211 and the second location 212 in the spirally-arranged protruding portion 21 is a planar shape (an outer peripheral surface 21*c*2 in a planar shape) or a concave shape (an outer peripheral surface 21*c*3 in a concave shape).

Specific examples of the spirally-arranged protruding portion 21 including the above-mentioned outer peripheral surface 21*c*2 in a planar shape may include the spirally-arranged protruding portion 21 formed so that the height t of the spirally-arranged protruding portion 21 at the first location 211 is linearly lowered from the proximal end of the first location 211 to the distal end of the first location 211 (see FIG. 4A), and the spirally-arranged protruding portion 21 formed so that the height t of the spirally-arranged protruding portion 21 at the second location 212 is linearly lowered from the distal end of the second location 212 to the proximal end of the second location 212 (see FIG. 4B).

Specific examples of the spirally-arranged protruding portion 21 including the above-mentioned outer peripheral surface 21*c*3 in a concave shape may include the spirally-arranged protruding portion 21 formed so that a decreasing rate of the height t of the spirally-arranged protruding portion 21 at the first location 211 (an amount of decrease in height t per unit length in a helical direction of the spirally-arranged protruding portion 21, the same applies hereinafter) gradually decreases from the proximal end of the first location 211 toward the distal end of the first location 211 (see FIG. 4C), and the spirally-arranged protruding portion 21 formed so that a decreasing rate of the height t of the spirally-arranged protruding portion 21 at the second location 212 gradually decreases from the distal end of the second location 212 toward the proximal end of the second location 212 (see FIG. 4D).

As described above, when in the dilator 1, the outer peripheral surface 21*c*2 in a planar shape or the outer peripheral surface 21*c*3 in a concave shape is provided in at least any one of the first location 211 and the second location 212 in the spirally-arranged protruding portion 21, it is possible to further reduce a contact resistance with a contact object when the dilator 1 is inserted or removed.

The spirally-arranged protruding portion 21 may be formed as a continuous or discontinuous single-thread or multi-thread projection. Further, the spirally-arranged protruding portion 21 may be formed integrally with or separately from the shaft 11.

In the dilator 1, the spirally-arranged protruding portion 21 is formed as a continuous single-thread projection, and the spirally-arranged protruding portion 21 and the shaft 11 (the distal end section 111, the tapered section 112, and the body section 113) are integrally formed by casting or the like.

A material for forming the spirally-arranged protruding portion 21 is not particularly limited as long as an effect of the disclosed embodiments is not impaired, and examples thereof may include a metallic material such as stainless steel and superelastic alloy (nickel-titanium alloy) and a resin material such as a polyamide resin and a fluororesin, which has biocompatibility.

It is preferable that the spirally-arranged protruding portion 21 does not form a cutting edge (does not have a shape that cuts a living tissue). That is, it is preferable that, in a shape of a transverse cross-section of the spirally-arranged protruding portion 21 (a cross-section orthogonal to a helical direction of the spirally-arranged protruding portion 21), an outer end of the shaft 11 in the radial direction (the outer peripheral surface of the spirally-arranged protruding portion 21) does not have an acute-angled corner section. An example of such an end includes a portion formed of an obtuse-angled corner and a shape including a curve (such as a curve including a part of a circle or an ellipse). This shape enables the dilator 1 to dilate a hole or the like of the target object without damaging a living tissue on an inner surface of the hole or the like of the target object.

The base section 31 is a section used by an operator to push the dilator 1 into a human body or perform a rotation operation of the dilator 1. The base section 31 has its distal end being connected to the proximal end of the body section 113, and includes a through-hole 31*h* communicating with the through-hole 11*h* of the shaft 11. During the operation, a guide wire or the like is inserted through the through-hole 31*h* of the base section 31.

As for a length in the axial direction in each section of the dilator 1, a whole of the shaft 11 may be from 1600 mm to 2500 mm, the distal end section 111 may be from 0 mm to 100 mm, and the tapered section 112 may be from 5 mm to 100 mm. As for an outer diameter in each section of the shaft 11, distal ends of the distal end section 111 and the tapered section 112 may be from 0.8 mm to 3.0 mm, and a proximal end of the tapered section 112 and the body section 113 may be from 1.4 mm to 5.0 mm. An inner diameter of the through-hole 11*h* of the shaft 11 may be from 0.4 mm to 1.0 mm. Heights t of the locations other than the first and second locations 211 and 212 in the spirally-arranged protruding portion 21 may be t=0.1 mm to 0.5 mm. Lengths in the helical direction of the first and second locations 211 and 212 may be from 0.1 mm to 5.0 mm, respectively.

As for a length in the axial direction in each section of the dilator 1, a whole of the shaft 11 is 2,000 mm, the distal end section 111 is 10 mm, and the tapered section 112 is 30 mm. As for an outer diameter of each section of the shaft 11, distal ends of the distal end section 111 and the tapered section 112 are 1.84 mm, and a proximal end of the tapered section 112 and the body section 113 are 2.64 mm. An inner diameter of the through-hole 11*h* of the shaft 11 is 0.7 mm. The height t of the spirally-arranged protruding portion 21 is t=0.36 mm. Lengths in the helical direction of the first and second locations 211 and 212 are 2.0 mm and 2.0 mm, respectively.

Next, an example of a usage mode of the dilator 1 will be described.

Firstly, a target object is punctured with an introducer needle (not illustrated) to form a hole. Next, after a guide wire (not illustrated) is inserted into a lumen of the introducer needle, the introducer needle is pulled out.

Next, the proximal end of the guide wire is inserted into the through-hole 11h of the dilator 1, the dilator 1 is pushed to a location such as a hole of the target object (hereinafter, also referred to as "punctured section"), and is inserted into the hole or the like of the target object from a distal end 11b of the shaft 11. Next, the shaft 11 is pushed forward while the shaft 11 is rotated. At this time, when the shaft 11 is pushed forward from the distal end section 111 to the body section 113 via the tapered section 112, the hole or the like of the target object has been dilated. It is noted that after the hole or the like of the target object is dilated, the shaft 11 is rotated in a direction opposite to a rotation direction in which the shaft 11 is inserted, and thus, it is possible to pull out the shaft 11 from the hole or the like of the target object.

As described above, the dilator 1 has the above configuration, and thus, when the shaft 11 is inserted into or removed from the hole or the like of the target object, it is possible to reduce the contact resistance with a contact object generated between the distal end and the proximal end of the spirally-arranged protruding portion 21 to advance and retreat the shaft 11 smoothly.

It is noted that in the dilator 1, the height t of the distal end of the first location 211 and the height t of the proximal end of the second location 212 may not satisfy t=0, and as illustrated in FIG. 4E, the height t may satisfy t>0 (in the radial direction of the shaft, a position of the spirally-arranged protruding portion and a position of an outer peripheral surface of the shaft at the distal end and the proximal end of the spirally-arranged protruding portion are separated, and as a result, the distal end and the proximal end protrude vertically toward an outside in the radial direction from the outer peripheral surface).

FIG. 5 is a partially cut schematic side view illustrating a part of a dilator of the disclosed embodiments. As illustrated in FIG. 5, dilator 2 generally includes the shaft 11, a spirally-arranged protruding portion 22, and the base section 31 (not illustrated). The dilator 2 is different from that in the dilator 1 in that the dilator 2 includes the spirally-arranged protruding portion 22. It is noted that the shaft 11 and the base section 31 are configured in the same way as the dilator 1, and thus, the same parts as those of the dilator 1 are designated by the same reference numerals, and detailed description thereof will not be repeated. Further, the spirally-arranged protruding portion 22 is configured in the same way, except for a shape, as the spirally-arranged protruding portion 21 in the dilator 1, and thus, the description thereof will not be repeated.

The spirally-arranged protruding portion 22 are provided on the outer peripheral surface 11a of each of the distal end section 111, the tapered section 112, and the body section 113, and include gaps 22a between neighboring sections of the spirally-arranged protruding portion 22 along the axial direction of the shaft 11. The spirally-arranged protruding portion 22 includes a location 221 (hereinafter, also referred to as "first location 221") at the distal end side in the spirally-arranged protruding portion 22 and a location 222 (hereinafter, also referred to as "second location 222") at the proximal end side in the spirally-arranged protruding portion 22. The location 221 includes the distal end of the spirally-arranged protruding portion 22 and the location 222 is located at a proximal end side relative to the first location 221 and includes the proximal end of the spirally-arranged protruding portion 22. A height of the spirally-arranged protruding portion 22 at the first location 221 gradually decreases toward the distal end side of the spirally-arranged protruding portion 22 along the spirally-arranged protruding portion 22. A height of the spirally-arranged protruding portion 22 at the second location 222 gradually decreases toward the proximal end side of the spirally-arranged protruding portion 22 along the spirally-arranged protruding portion 22.

In the dilator 2, the distal end of the spirally-arranged protruding portion 22 is distant from the distal end of the shaft 11 in the axial direction. Specifically, a distal end 22b of the spirally-arranged protruding portion 22 is distant from the distal end 11b of the shaft 11 toward the proximal end side by a predetermined distance L, and the shaft 11 includes a region in the distal end section 111 not including the spirally-arranged protruding portion 22 on the outer peripheral surface 11a (hereinafter, also referred to as "protrusion non-formed section"). The predetermined distance L described above is not particularly limited as long as the effect of the disclosed embodiments is not impaired, and may employ for example, a dimension or the like having the same length as the outer diameter of the distal end section 111.

As described above, in the dilator 2, the distal end 22b of the spirally-arranged protruding portion 22 is distant from the distal end 11b of the shaft 11 in the axial direction, and thus, for example, when the shaft 11 is inserted into the hole or the like of the target object from the distal end 11b of the shaft 11, the spirally-arranged protruding portion 22 is guided by the previously inserted protrusion non-formed section, which ensures easy and infallible engagement of the spirally-arranged protruding portion 22 with a punctured section.

FIG. 6 is a schematic side view entirely illustrating a dilator of the disclosed embodiments. As illustrated in FIG. 6, dilator 3 generally includes a shaft 13, a spirally-arranged protruding portion 23, and the base section 31. In the dilator 3, the shaft 13 and the spirally-arranged protruding portion 23 are different from those in the dilator 1. It is noted that the base section 31 is configured in the same way as the dilator 1, and thus, the same parts as those of the dilator 1 are designated by the same reference numerals, and detailed description thereof will not be repeated. Further, the shaft 13 and the spirally-arranged protruding portion 23 are configured in the same way, except for a shape, as the shaft 11 and the spirally-arranged protruding portion 21 in the dilator 1, respectively, and thus, the description thereof will not be repeated.

The shaft 13 is a hollow-shaped member. The shaft 13 includes a distal end section 131, a tapered section 132, a body section 133, and a through-hole 13h. The tapered section 132 is a section of which the outer diameter at the distal end is smaller than an outer diameter at the proximal end. The distal end section 131 is a section of which a proximal end is located at the distal end of the tapered section 132, and which extends toward a distal end side in an axial direction of the tapered section 132. The body section 133 is a section of which a distal end is located at the proximal end of the tapered section 132 and which extends toward the proximal end side in the axial direction of the tapered section 132. The through-hole 13h is a hollow-shaped section.

The shaft 13 of the dilator 3 is formed of a first coil body 13c formed by winding a wire around an axis of the shaft 13. Specifically, for example, the first coil body 13c is formed by helically winding one or more wires so that adjacent wires are in close contact with one another in the axial direction. The first coil body 13c is divided into the above-mentioned distal end section 131, tapered section 132, and body section 133 according to a shape of an outer peripheral surface 13a of the first coil body 13c. It is noted that in FIG. 6, an internal common tangent of the first coil body 13c is illustrated by a broken line, and the through-hole 13h is formed in a region surrounded by the internal common tangent.

The spirally-arranged protruding portion 23 are provided on the outer peripheral surface 13a of each of the distal end section 131, the tapered section 132, and the body section 133, and include gaps 23a between neighboring sections of the spirally-arranged protruding portion 23 along the axial direction of the shaft 13. The spirally-arranged protruding portion 23 includes a location 231 (hereinafter, also referred to as "first location 231") at the distal end side in the spirally-arranged protruding portion 23 and a location 232 (hereinafter, also referred to as "second location 232") at the proximal end side in the spirally-arranged protruding portion 23. The location 231 includes the distal end of the spirally-arranged protruding portion 23 and the location 232 is located at the proximal end side relative to the first location 231 and includes the proximal end of the spirally-arranged protruding portion 23. A height of the spirally-arranged protruding portion 23 at the first location 231 gradually decreases toward the distal end side of the spirally-arranged protruding portion 23 along the spirally-arranged protruding portion 23. A height of the spirally-arranged protruding portion 23 at the second location 232 gradually decreases toward the proximal end side of the spirally-arranged protruding portion 23 along the spirally-arranged protruding portion 23.

The spirally-arranged protruding portion 23 of the dilator 3 is formed of a second coil body 23c formed by winding one or more wires around the outer peripheral surface 13a of the shaft 13. In the second coil body 23c, the height of the spirally-arranged protruding portion 23 at the first location 231 (for example, an outer diameter of the wire of the second coil body 23c) gradually decreases toward the distal end side of the second coil body 23c along the wire of the second coil body 23c. Further, in the second coil body 23c, the height of the spirally-arranged protruding portion 23 at the second location 232 (for example, an outer diameter of the wire of the second coil body 23c) gradually decreases toward the proximal end side of the second coil body 23c along the wire of the second coil body 23c.

Specifically, as illustrated in FIGS. 7A and 7B, the height t of the spirally-arranged protruding portion 23 at the first location 231 may be formed so that the height t gradually decreases from the proximal end of the first location 231 toward a distal end 23b of the first location 231 (an outer peripheral surface 23c1 in a convex shape).

On the other hand, specifically, as illustrated in FIGS. 8A and 8B, the height t of the spirally-arranged protruding portion 23 at the second location 232 may be formed so that the height t gradually decreases from a distal end of the second location 232 toward a proximal end of the second location 232 (the outer peripheral surface 23c1 in a convex shape).

Examples of a method of adjusting the height t of the spirally-arranged protruding portion 23 include a method of drawing the wire only at ends (the first location 231 and the second location 232) of the second coil body 23c so that the ends are reduced in diameter toward the distal end and the proximal end, and a method of polishing only ends (the first location 231 and the second location 232) of the second coil body 23c toward the distal end and the proximal end in a tapered shape.

Here, the diameter of the wire for forming the first coil body 13c may be from 0.1 mm to 0.5 mm, and the diameter of the wire for forming the second coil body 23c (diameters of locations other than the first and second locations 231 and 232) may be from 0.1 mm to 0.5 mm. Lengths in the helical direction of the first and second locations 231 and 232 may be from 0.1 mm to 5.0 mm, respectively.

In the dilator 3, the diameter of the wire of the first coil body 13c is 0.21 mm. The diameters of locations other than the first and second locations 231 and 232 of the second coil body 23c are 0.36 mm, and lengths in the helical direction of the first and second locations 231 and 232 are 2.0 mm and 2.0 mm, respectively. Further, in the first and second locations 231 and 232, the height t of the spirally-arranged protruding portion 23 is adjusted by polishing the wire, and the heights of the distal end and the proximal end of the second coil body 23c are formed so that t=0 is satisfied.

Examples of a material of the wire for forming the first coil body 13c and the second coil body 23c may include materials similar to those exemplified as the materials in the dilator 1 for forming the distal end section 111, the tapered section 112, and the body section 113, and the spirally-arranged protruding portion 21 respectively.

Examples of a method of joining the first coil body 13c and the second coil body 23c may include a method of brazing the first coil body 13c and the second coil body 23c at both ends of the second coil body 23c, a method of welding the same, a method of fixing the same with an adhesive, and a method of depositing the same through a coating. In the dilator 3, the first coil body 13c and the second coil body 23c are brazed at the both ends of the second coil body 23c.

As described above, in the dilator 3, the shaft 13 and the spirally-arranged protruding portion 23 are formed of the first coil body 13c and the second coil body 23c, respectively, and thus, it is possible to improve a flexibility and a torquability in each of the shaft 13 and the spirally-arranged protruding portion 23 and to improve a flexibility and a torquability in the dilator 3 by the combination of the first coil body 13c and the second coil body 23c.

The disclosed embodiments are not limited to the configuration of the above-described embodiments, but is indicated by the claims, and is intended to include all modifications within meanings and the scope equivalent to the claims.

For example, in the above-described embodiments, description is given of the dilators 1 to 3 in which in all of the first locations 211, 221, and 231 and the second locations 212, 222, and 232, the heights of the spirally-arranged protruding portion gradually decrease, but it may suffice that the dilators include the spirally-arranged protruding portion of which the height gradually decreases at at least any one of the first location or the second location, and for example, and may be a dilator in which the height of the spirally-arranged protruding portion at the first location only gradually decreases and a dilator in which the height of the spirally-arranged protruding portion at the second location only gradually decreases, of the first location and the second location.

Further, in the dilator 3, description is given of the dilator in which the spirally-arranged protruding portion 23 includes the outer peripheral surface 23c1 in a convex shape, but a dilator may be employed in which an outer peripheral surface (not illustrated) in a planar shape or an outer peripheral surface in a concave shape is included, as described above.

Further, in the dilators 1, 2 described above, description is given of the dilators in which the shaft 11 and the spirally-arranged protruding portion 21 and 22 are integrally formed, and in the dilator 3, description is given of the dilator in which the shaft 13 and the spirally-arranged protruding portion 23 are formed of the first coil body 13c and the second coil body 23c, respectively, but for example, the dilator may be a dilator 5m1 (see FIG. 9) in which a shaft 15m1 (a distal end section, a tapered section, and a body section) is formed integrally and a spirally-arranged protruding portion 25m1 is formed of the second coil body.

Further, in the dilator 2 described above, description is given of the dilator in which the shaft 11 and the spirally-arranged protruding portion 22 are integrally formed and the distal end 22b of the spirally-arranged protruding portion 22 is distant from the distal end 11b of the shaft 11 in the axial direction, but for example, a dilator 5m2 (see FIG. 10A) in which a shaft 15m2 and a spirally-arranged protruding portion 25m2 are formed of the first and second coil bodies, respectively, and a distal end 25cbm2 of the second coil body is distant from a distal end 15cbm2 of the first coil body in the axial direction, and a dilator 5m3 (see FIG. 10B) in which a shaft 15m3 is integrally formed and a spirally-arranged protruding portion 25m3 is formed of the second coil body and a distal end 25cbm3 of the second coil body is distant from a distal end 15cbm3 of the shaft 15m3 in the axial direction, also fall within the scope of the present disclosure.

Further, in the dilators 1 to 3 described above, description is given of the dilators in which the shafts 11 and 13 include the distal end sections 111 and 131, the tapered sections 112 and 132, and the body sections 113 and 133, but a dilator may be employed in which the shaft does not include the distal end section but includes the tapered section and the body section only. Examples of such a dilator include a dilator 5m4 (see FIG. 11A) in which a shaft 15m4 including a tapered section 152m4 and a body section 153m4 and a spirally-arranged protruding portion 25m4 are integrally formed, a dilator 5m5 (see FIG. 12A) in which a shaft 15m5 including a tapered section 152m5 and a body section 153m5 and a spirally-arranged protruding portion 25m5 are formed of a coil body (first and second coil bodies), and dilators 5m6 and 5m7 (see FIGS. 11B and 12B) with a separation by predetermined distances Lm6 and Lm7 from the distal end of the tapered sections 152m6 and 152m7 toward the proximal end side thereof. Further, although not illustrated, in such a dilator, a shaft may be integrally formed and a spirally-arranged protruding portion may be formed of a second coil body. The dilator also exhibits an effect similar to that in the dilators 1 to 3 described above.

The invention claimed is:

1. A dilator comprising:
   a hollow-shaped shaft comprising (i) a tapered section with an outer diameter of a distal end being smaller than an outer diameter of a proximal end, (ii) a distal end section including a proximal end being located at the distal end of the tapered section and extending toward a distal end side of the tapered section in an axial direction, and (iii) a body section including a distal end being located at the proximal end of the tapered section and extending toward a proximal end side of the tapered section in the axial direction; and
   a spirally-arranged protruding portion comprising (i) spirally-arranged protruding sections provided on outer peripheral surfaces of each of the tapered section, the distal end section, and the body section, and (ii) gaps between adjacent spirally-arranged protruding sections along the axial direction of the shaft,
   wherein a location being at a terminal distal end side of the spirally-arranged protruding portion and including a distal end of the spirally-arranged protruding portion is a first location and a location being at a proximal end side of the spirally-arranged protruding portion and at the proximal end side relative to the first location and including a proximal end of the spirally-arranged protruding portion is a second location,
   at least one of (i) a height of the spirally-arranged protruding portion at the first location gradually decreases toward the distal end side of the spirally-arranged protruding portion, and (ii) a height of the spirally-arranged protruding portion at the second location gradually decreases toward the proximal end side of the spirally-arranged protruding portion, and
   a shape of an outer peripheral surface at at least one of the first location and the second location in the spirally-arranged protruding portion is a concave shape.

2. The dilator according to claim 1, wherein the shaft is formed of a coil body formed by winding a wire around an axis of the shaft.

3. The dilator according to claim 1, wherein the spirally-arranged protruding portion is formed of a coil body formed by winding a wire on an outer peripheral surface of the shaft.

4. The dilator according to claim 1, wherein the distal end of the spirally-arranged protruding portion is spaced apart from the distal end of the shaft in the axial direction.

5. A dilator comprising:
   a hollow-shaped shaft comprising (i) a tapered section with an outer diameter of a distal end being smaller than an outer diameter of a proximal end, (ii) a distal end section including a proximal end being located at the distal end of the tapered section and extending toward a distal end side of the tapered section in an axial direction, and (iii) a body section including a distal end being located at the proximal end of the tapered section and extending toward a proximal end side of the tapered section in the axial direction; and
   a spirally-arranged protruding portion comprising (i) spirally-arranged protruding sections provided on outer peripheral surfaces of each of the tapered section, the distal end section, and the body section, and (ii) gaps between adjacent spirally-arranged protruding sections along the axial direction of the shaft,
   wherein a location being at a terminal distal end side of the spirally-arranged protruding portion and including a distal end of the spirally-arranged protruding portion is a first location and a location being at a proximal end side of the spirally-arranged protruding portion and at the proximal end side relative to the first location and including a proximal end of the spirally-arranged protruding portion is a second location,
   at least one of (i) a height of the spirally-arranged protruding portion at the first location gradually decreases toward the distal end side of the spirally-arranged protruding portion, and (ii) a height of the spirally-arranged protruding portion at the second location gradually decreases toward the proximal end side of the spirally-arranged protruding portion,
   the body section includes a straight part with a constant outer diameter, the straight part having a distal end located at the proximal end of the tapered section and extending toward a proximal end side of the body section in the axial direction, the spirally-arranged protruding portion extends continuously from the tapered section through to the straight part and a shape of an outer peripheral surface at at least one of the first location and the second location in the spirally-arranged protruding portion is a concave shape.

6. The dilator according to claim 5, wherein a shape of an outer peripheral surface of at least one of the first location and the second location in the spirally-arranged protruding portion is a planar shape.

7. The dilator according to claim 5, wherein the shaft is formed of a coil body formed by winding a wire around an axis of the shaft.

8. The dilator according to claim 5, wherein the spirally-arranged protruding portion is formed of a coil body formed by winding a wire on an outer peripheral surface of the shaft.

9. The dilator according to claim 5, wherein the distal end of the spirally-arranged protruding portion is spaced apart from the distal end of the shaft in the axial direction.

10. The dilator according to claim 5, wherein a shape of an outer peripheral surface of at least one of the first location and the second location in the spirally-arranged protruding portion is a concave shape.

11. A dilator comprising:

a hollow-shaped shaft formed of a coil body formed by winding a wire around an axis of the shaft, and comprising (i) a tapered section with an outer diameter of a distal end being smaller than an outer diameter of a proximal end, (ii) a distal end section including a proximal end being located at the distal end of the tapered section and extending toward a distal end side of the tapered section in an axial direction, and (iii) a body section including a distal end being located at the proximal end of the tapered section and extending toward a proximal end side of the tapered section in the axial direction; and a spirally-arranged protruding portion comprising (i) spirally-arranged protruding sections provided on outer peripheral surfaces of each of the tapered section, the distal end section, and the body section, and (ii) gaps between adjacent spirally-arranged protruding sections along the axial direction of the shaft, wherein a location being at a distal end side of the spirally-arranged protruding portion and including a distal end of the spirally-arranged protruding portion is a first location and a location being at a proximal end side of the spirally-arranged protruding portion and at the proximal end side relative to the first location and including a proximal end of the spirally-arranged protruding portion is a second location, the spirally-arranged protruding portion directly contacts the coil body, and at least one of (i) a height of the spirally-arranged protruding portion at the first location gradually decreases toward the distal end side of the spirally-arranged protruding portion, and (ii) a height of the spirally-arranged protruding portion at the second location gradually decreases toward the proximal end side of the spirally-arranged protruding portion.

12. The dilator according to claim 11, wherein a shape of an outer peripheral surface of at least one of the first location and the second location in the spirally-arranged protruding portion is a planar shape.

13. The dilator according to claim 11, wherein the spirally-arranged protruding portion is formed of a coil body formed by winding a wire on an outer peripheral surface of the shaft.

14. The dilator according to claim 11, wherein the distal end of the spirally-arranged protruding portion is spaced apart from the distal end of the shaft in the axial direction.

15. The dilator according to claim 11, wherein a shape of an outer peripheral surface of at least one of the first location and the second location in the spirally-arranged protruding portion is a concave shape.

* * * * *